(12) United States Patent
Pior et al.

(10) Patent No.: US 6,432,073 B2
(45) Date of Patent: Aug. 13, 2002

(54) FOOT ORTHOSIS

(75) Inventors: James Pior, Monument Beach, MA (US); Mark T. Ingersoll, Atascadero, CA (US); Charles Hare, Arroyo Grande, CA (US); Richard D. Curley, Jr., Atascadero, CA (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 09/770,341

(22) Filed: Jan. 26, 2001

Related U.S. Application Data

(63) Continuation-in-part of application No. 09/472,706, filed on Dec. 23, 1999.

(51) Int. Cl.[7] ................................................. A61F 5/00
(52) U.S. Cl. ............................ 602/10; 602/27; 128/882
(58) Field of Search ................................ 128/846, 869, 128/882; 602/23, 16, 27, 28

(56) References Cited

U.S. PATENT DOCUMENTS

| | | |
|---|---|---|
| 1,473,506 A | 11/1923 | Nessler |
| 1,567,931 A | 12/1925 | Epler |
| 1,927,751 A | 9/1933 | Mensi |
| 1,964,962 A | 7/1934 | Rosenblum |
| 3,802,424 A | 4/1974 | Newell |
| 3,878,626 A | 4/1975 | Isman |
| 4,446,856 A | 5/1984 | Jordan |
| D323,239 S | 1/1992 | Rooke |
| 5,088,479 A | 2/1992 | Detoro |
| 5,143,058 A | 9/1992 | Luber et al. |
| 5,154,695 A | 10/1992 | Farris et al. |
| D338,067 S | 8/1993 | Luber et al. |
| 5,330,419 A | 7/1994 | Toronto et al. |
| D351,912 S | 10/1994 | Turtzo et al. |
| D363,780 S | 10/1995 | Darby et al. |
| 5,496,358 A | 3/1996 | Rosenwald |
| D375,164 S | 10/1996 | Wasserman et al. |
| 5,569,173 A | 10/1996 | Varn |
| D388,174 S | 12/1997 | Stano |
| 5,741,220 A | 4/1998 | Brink |
| D395,514 S | 6/1998 | Stano |
| 5,799,659 A | 9/1998 | Stano |
| D412,581 S | 8/1999 | Brennan |

OTHER PUBLICATIONS

Theraboot™ Therapeutic Orthotic System from Orthotic Rehabilitation Products, Inc. Tampa, FL (Jan. 1994).

*Primary Examiner*—Michael A. Brown
(74) *Attorney, Agent, or Firm*—Luedeka, Neely & Graham PC

(57) ABSTRACT

An orthosis including a splint, a sole member detachably connectable to a surface of the splint, a fastener extending from the surface of the splint, an aperture extending through the sole member for receiving the fastener, a projection extending from the surface of the splint and spaced apart from the fastener, and a receptacle defined on the sole member for receiving the projection in a snap-fit relationship when the sole member is installed on the splint.

10 Claims, 22 Drawing Sheets

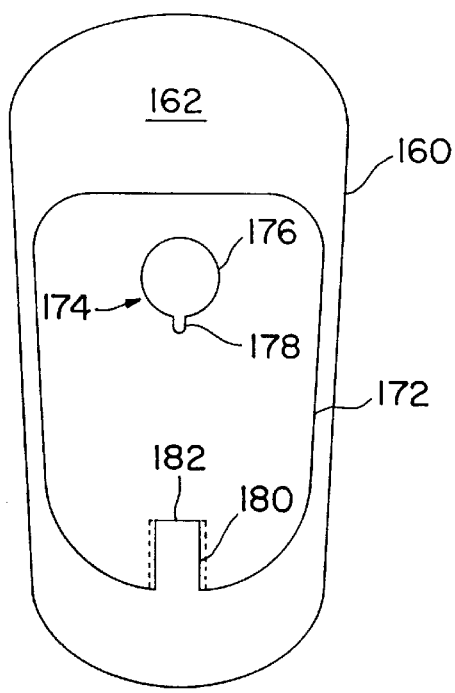
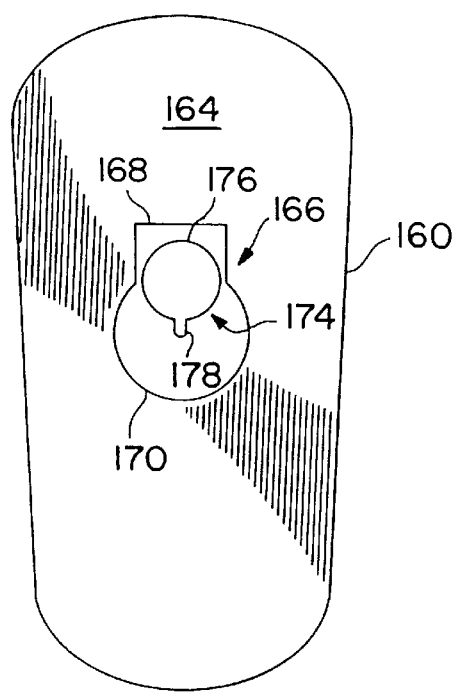
FIG. 15  FIG. 16
FIG. 17

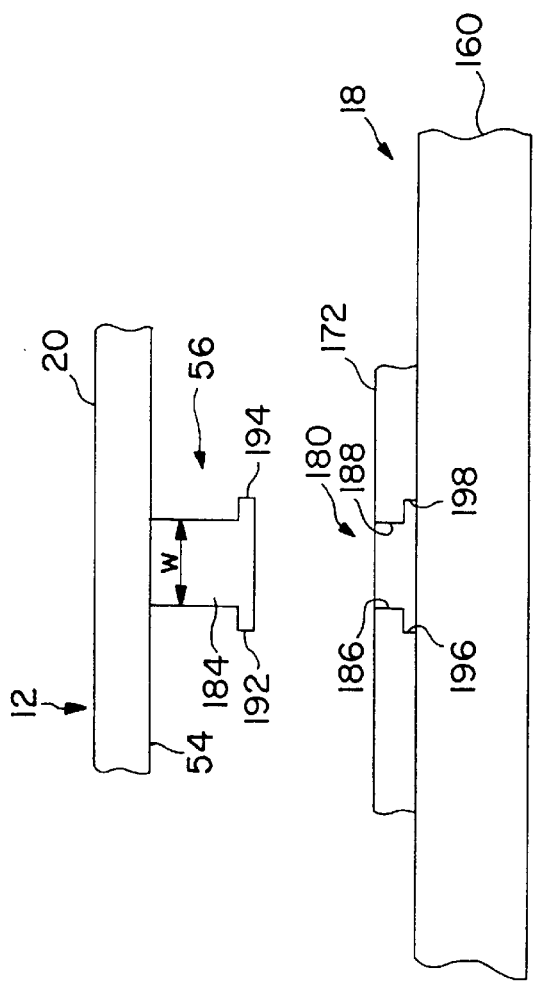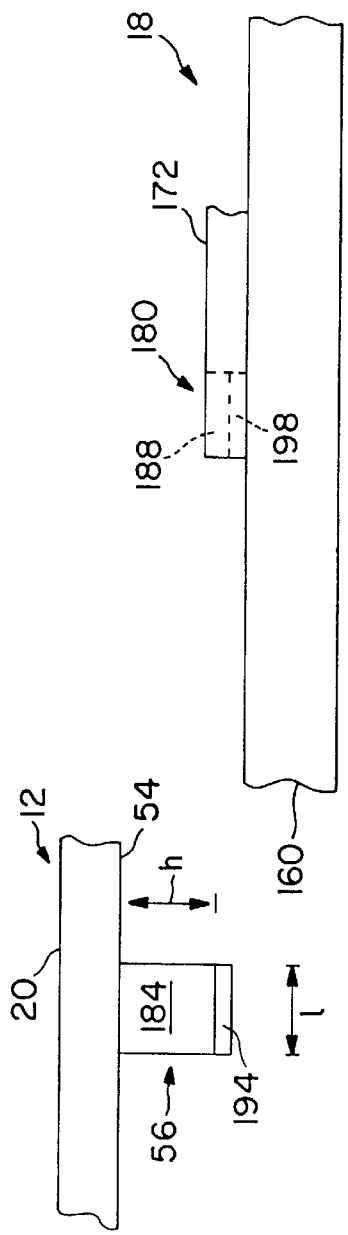
FIG. 18a
FIG. 18b

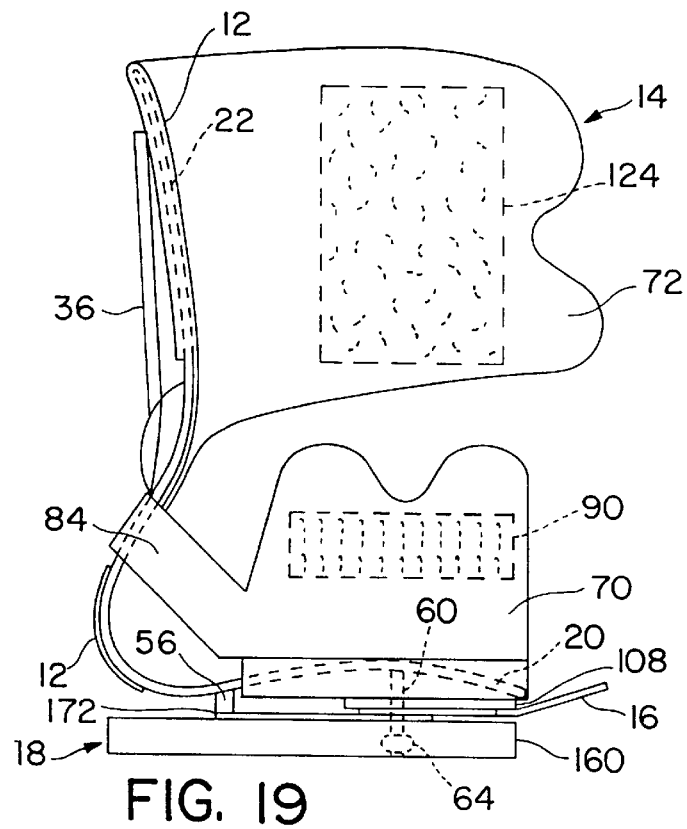
FIG. 19
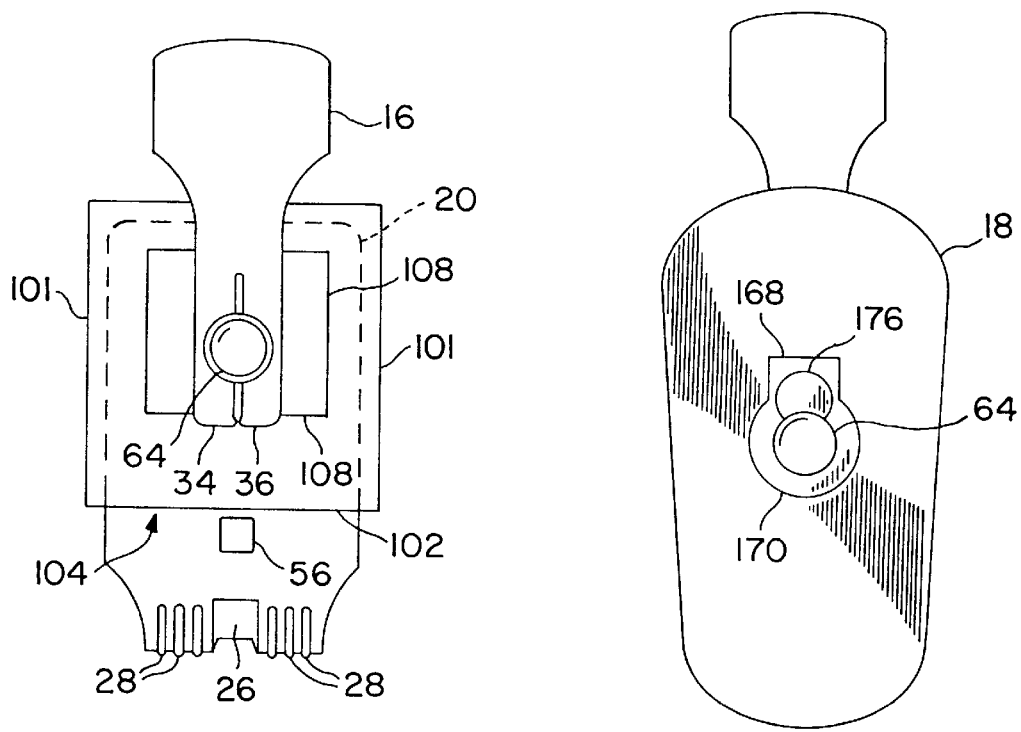
FIG. 21
FIG. 20

FOOT ORTHOSIS

CROSS-REFERENCE TO RELATED APPLICATION

This is a continuation-in-part of pending U.S. application Ser. No. 09/472,706, filed Dec. 23, 1999, and entitled FOOT ORTHOSIS.

FIELD OF THE INVENTION

This invention relates generally to orthotic devices. More particularly, this invention relates to foot orthosis having detachable floor-contact devices.

BACKGROUND AND SUMMARY OF THE INVENTION

Prior art foot orthosis generally include an L-shaped plastic splint for supporting a patient's foot in a certain orientation, and a soft bootie that fits around the patient's foot, ankle and lower leg, and attaches to the splint to secure the foot, ankle and leg of the patient to the splint. Foot orthosis are used primarily on patients in hospitals and long-term care facilities.

Infection control regulations in place for a number of years have required that the bottom of orthosis be covered while the patient is walking to and from the bed, and that the covering be removed before reentering the bed. The purpose of this has been to limit contamination of the bed environment by floor-borne bacteria, etc. which might otherwise be picked up on the bottom surface of the orthosis. Attempts have been made to provide a sole member that can be installed on the bottom of the orthosis for floor contact and then removed before the patient reenters the bed. However, these soles members are generally difficult to install and remove, especially for a person not of good health. Also, such sole members have a tendency to detach from the orthosis during ambulation.

Accordingly, the invention relates to an improved foot orthosis having a removable sole member.

In a preferred embodiment, the foot orthosis includes a sole member detachably connectable to a surface of the splint, a fastener extending from the surface of the splint, an aperture extending through the sole member for receiving the fastener, a projection extending from the surface of the splint and spaced apart from the fastener, and a receptacle defined on the sole member for receiving the projection in a snap-fit relationship when the sole member is installed on the splint.

In another aspect, the invention relates to a pouch removably attachable to the splint for receiving a thermal (e.g., hot or cold) pack.

In a preferred embodiment, the pouch includes a first portion of material and a second portion of material having adjacent sides thereof secured together to define a pocket configured to receive the thermal pack through an opening thereof defined between unsecured edges of the first and second portions of material. The first portion of material has a length greater than the length of the second portion of material to define a lid portion positionable over the opening. A portion of hook material is attached to the first portion of material so that the pouch can be releasably attached to the splint covering material.

BRIEF DESCRIPTION OF THE DRAWINGS

Further advantages of the invention will become apparent by reference to the detailed description of preferred embodiments when considered in conjunction with the figures, which are not to scale, wherein like reference numbers, indicate like elements through the several views, and wherein.

FIG. 15 is a top plan view of a sole member suitable for use in the orthosis of the present invention;

FIG. 16 is a bottom plan view of the sole member of FIG. 15;

FIG. 17 is a side plan view of the sole member of FIG. 15;

FIGS. 18a and 18b are detailed end and side views showing structure for inhibiting relative movement as between the sole member and the splint of the orthosis FIG. 19 is a side plan view of the foot orthosis of FIG. 1;

FIG. 20 is a bottom plan view of the orthosis of FIG. 18, partially assembled to show the bootie positioned over the splint thereof;

FIG. 21 is a bottom plan view of the orthosis of FIG. 18, showing the sole member installed thereon;

DETAILED DESCRIPTION

Figure 1:
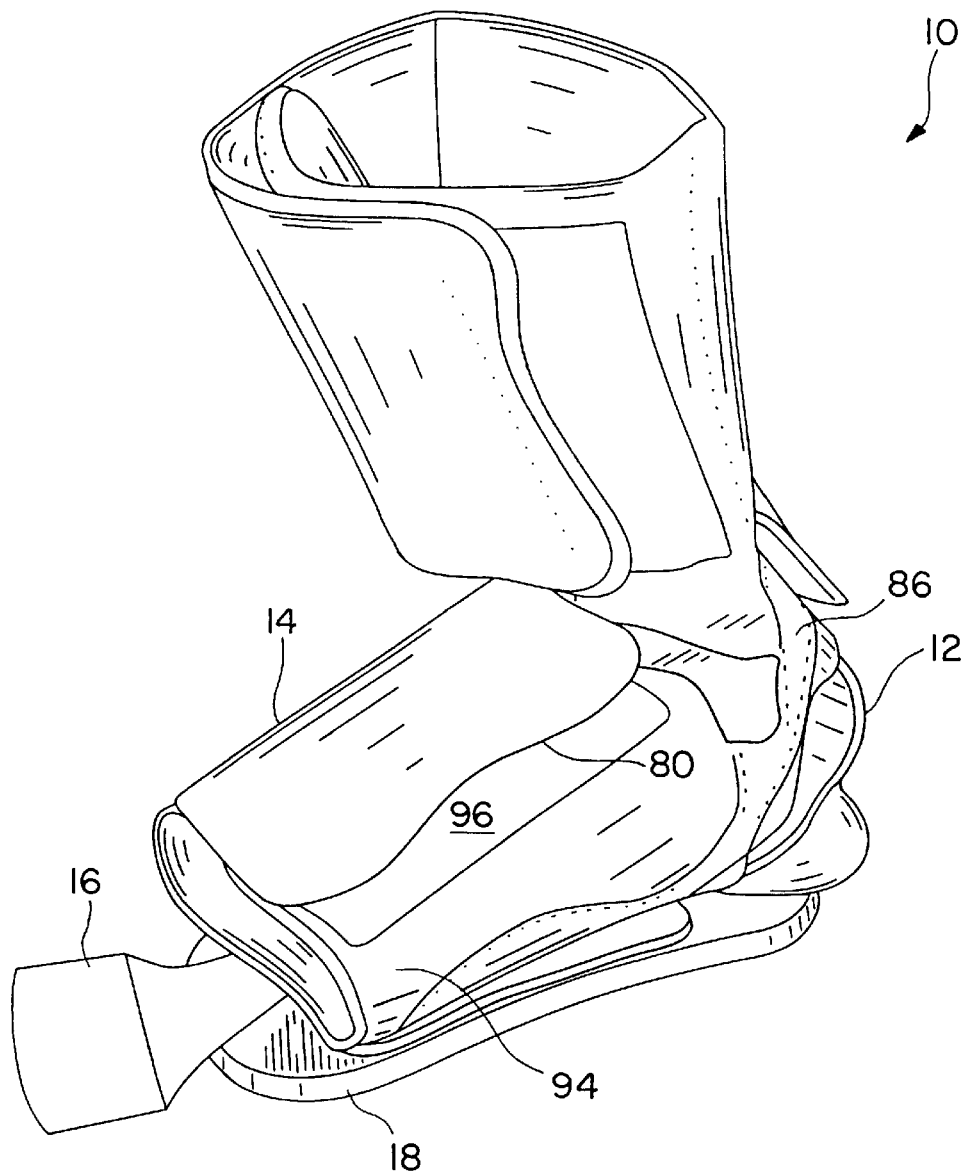
FIG. 1 is a perspective view of a foot orthosis in accordance with a preferred embodiment of the invention.
Figure 2:
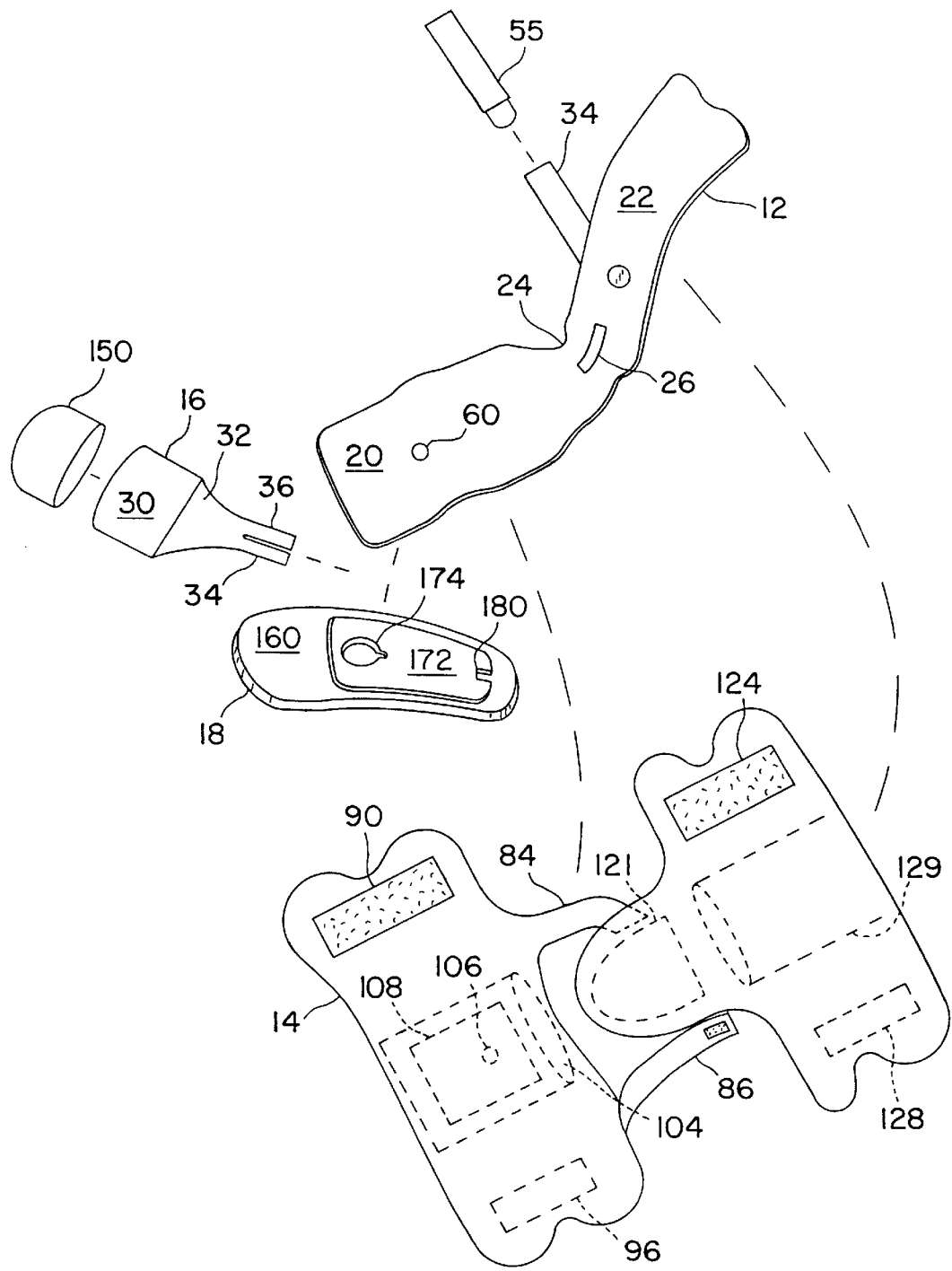
FIG. 2 is an exploded perspective view of the orthosis of FIG. 1.

With initial reference to FIGS. 1 and 2, the invention relates to a foot orthosis 10 having an L-shaped splint 12, a soft bootie 14, a toe support 16 and a sole member 18. The splint 12 supports a patient's foot in a certain orientation. The bootie 14 fits around the patient's foot, ankle and lower leg, and attaches to the splint 12 to secure the foot, ankle and leg of the patient to the splint 12. The toe support 16 attaches to the splint 12 to support the toes of the patient so that the front portion of the patient's foot does not hang down over the front of the orthosis. The sole member 18 can be readily installed on the bottom of the splint 10 for floor contact and then removed before the patient reenters the bed

Splint 12

With additional reference to FIGS. 3–6, the splint 12 is preferably of one-piece molded plastic construction and generally L-shaped in configuration. Preferred plastic materials are substantially rigid yet enable some flexure for patient comfort, particularly during ambulation. Preferred plastic materials include ABS plastic and polypropylene. The splint 12 is preferably of substantially uniform thickness, ranging from about ⅛ to about ¼ inches, most preferably about 3/16 inches.

Figure 3:
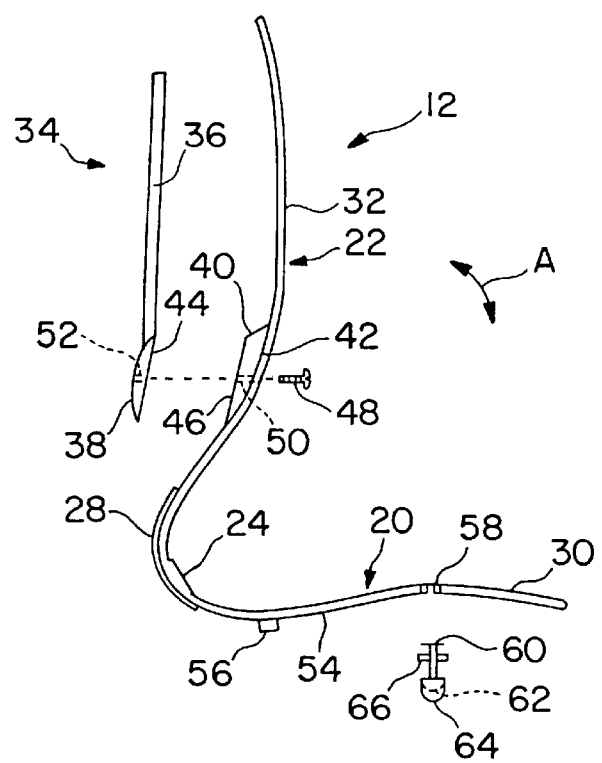
FIG. 3 is an exploded side plan view showing a splint suitable for use in the orthosis of the present invention.
Figure 4:
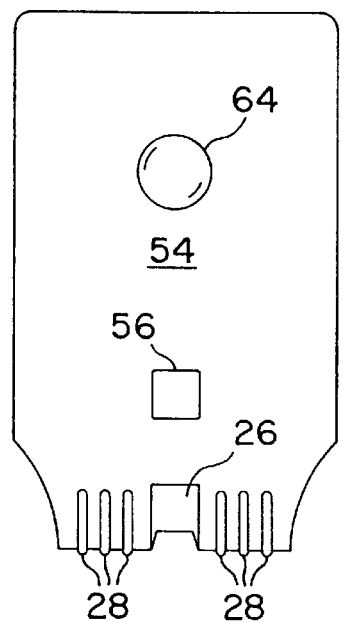
FIG. 4 is a bottom plan view of the splint of FIG. 3.

To provide the desired rigidity/flexure characteristics, the splint 12 preferably includes a foot contacting portion 20 and a leg contacting portion 22 oriented generally perpendicular to one another and connected by a bend 24. The foot contacting portion 20 and the leg contacting portion 22 are substantially rigid across their length and width, with the bend 24 configured to enable the portions 20 and 22 to be flexed toward and away from one another in the direction of the arrow A (FIG. 3). In this regard, the bend 24 preferably includes an elongate aperture 26 centrally located thereon to enhance flexibility and a plurality of raised ribs 28 integrally molded on exterior surfaces of the splint (relative to the patient's foot and leg) on opposite sides of the aperture 26 to reinforce the bend against breakage. The aperture 26 also provides a path to enable air to flow to the patient's foot.

The foot contacting portion 20 has a foot contact surface 30 that, while substantially flat, includes a small degree of convexity to conform generally to the arch of the patient's foot. Likewise, the leg contacting portion 22 includes a leg contact surface 32 that is somewhat concave to conform to the relatively semi-circular topography of the back of the patient's lower leg, mainly the calf muscle.

It has been experienced that patients tend to relax their leg muscles, particularly when sleeping, and roll their legs so that the side of their foot contacts the bed. To inhibit this, the splint 12 preferably includes a leg support 34 that can be positioned in an orientation substantially perpendicular to the patient's leg to inhibit the foot from rolling toward the bed.

The support 34 preferably includes an extension 36 having a substantially rectangular configuration with a length of from about 4 to about 8 inches, most preferably about 6 inches, and a width of from about ½ to about ½ inches, most preferably about 1 inch. A plurality of apertures 37 may be provided along the extension 36 for connection to other devices. For example, in some circumstances, a patient may wear a splint on each foot. If it is desired that the patient's hips or legs be substantially immobilized, the splints may be locked together as by an anti-rotation bar extending between the splints and connected to each splint via the apertures 37.

A mount 38 is provided for rotatably mounting one end of the extension 36 to the leg contacting portion 22 of the splint 12 opposite the leg of the patient. In this regard, a raised mounting surface 40 is provided on outer surface 42 of the leg contacting portion 22 just above the bend 24. The mount 38 and the surface 40 preferably have mating flat surfaces 44 and 46, respectively, that are maintained closely adjacent one another by a fastener, such as screw 48. The screw 48 passes through an aperture 50 that extends between the surfaces 32 and 46 and is threadably received by a threaded bore 52 in the mount 38. The mount 38 and the surface 40 preferably have rounded exposed surfaces so as to avoid hanging on the patient's clothing, sheeting and the like. A padded covering 55 preferably slips over the extension 36.

Figure 6:
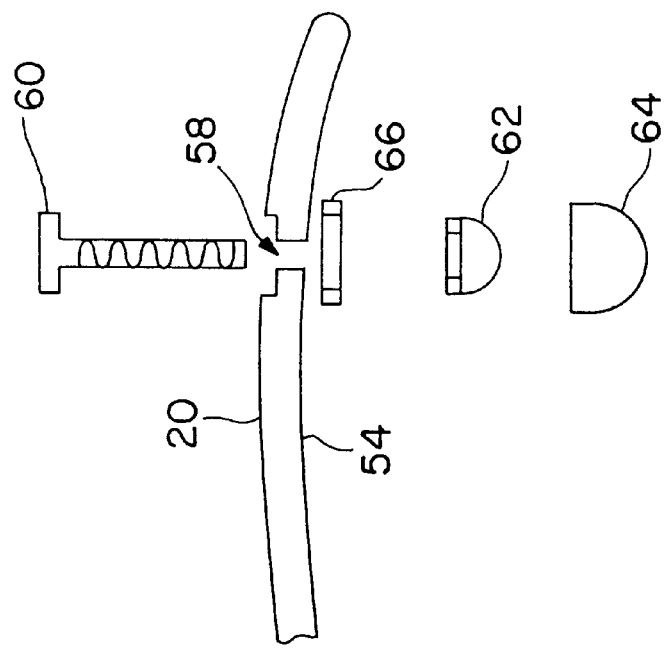
FIG. 6 is an exploded close-up view of a portion of the splint of FIG. 3.
Figure 5:
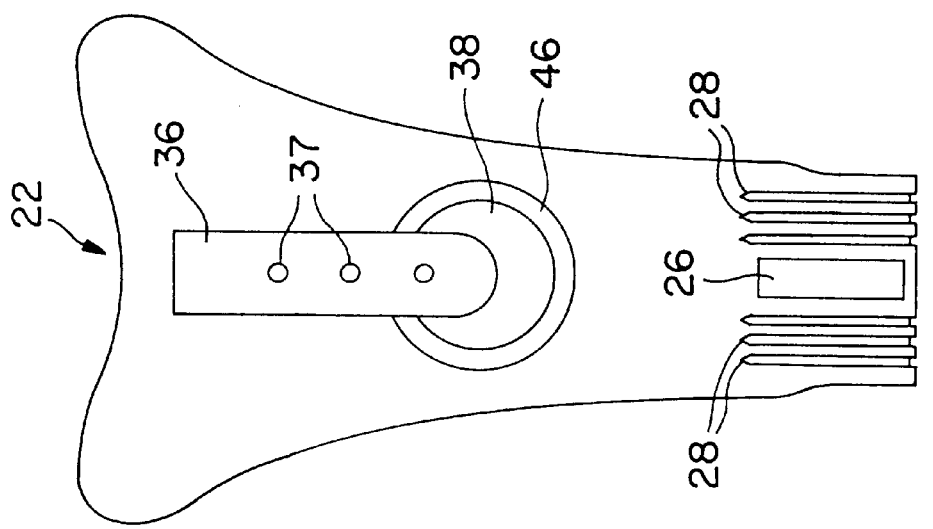
FIG. 5 is a rear plan view of the splint of FIG. 3.
Figure 7:
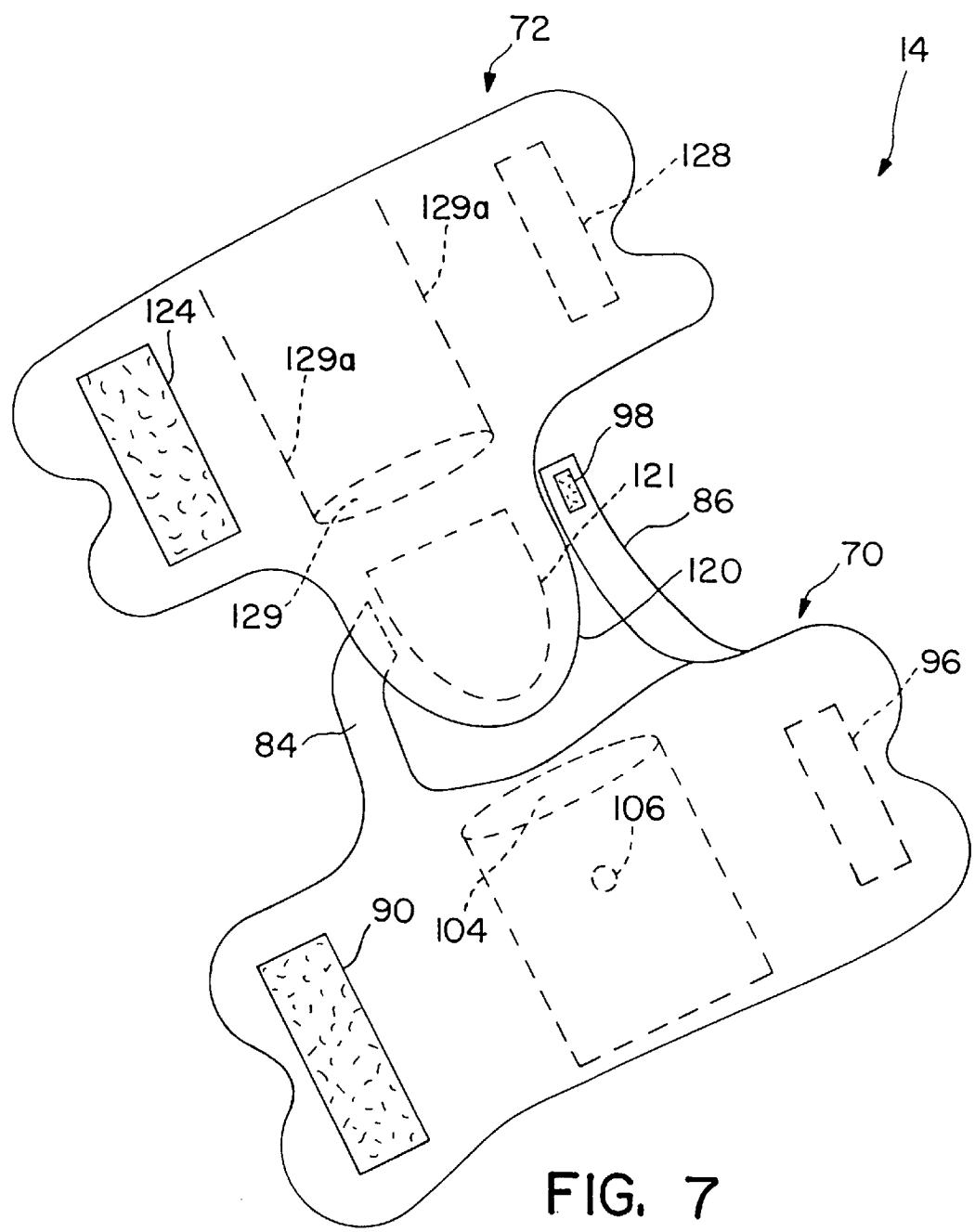
FIG. 7 is a perspective view of a soft bootie suitable for use in the orthosis of the present invention.

To facilitate releasable attachment of the sole member 18 to the splint 12, 15 lower surface 54 of the foot contacting portion 20 preferably includes a raised element, such as a square raised projection or nib 56 for engaging a conforming receptacle on the sole member 18, discussed in more detail below in connection with FIGS. 1 8a and 18b. Also, an aperture 58 extends between surfaces 30 and 54 of the foot contacting portion 20 for receiving a mounting bolt 60 onto which is threaded an end nut 62 having a plastic material or covering 64 molded thereon to provide a non-skid, padded covering. A locking nut 66 secures the bolt 60 within the aperture 58 (FIG. 6).

Soft Bootie 14

Turning to FIGS. 7–10, the bootie 14 is configured to fit around the patient's foot, ankle and lower leg, and attaches to the splint 12 to secure the foot, ankle and leg of the patient to the splint 12. The bootie 14 is preferably made of a soft fabric material such as fleece or a so-called "vel-foam" material available from Velcro USA of Manchester, N.H. If desired, exterior portions of the bootie may be reinforced with a nylon material, as discussed below. A preferred nylon material is a 430 denier pack cloth available from Rain Shed Outdoor Fabrics of Corvallis, Oregon.

Figure 8:
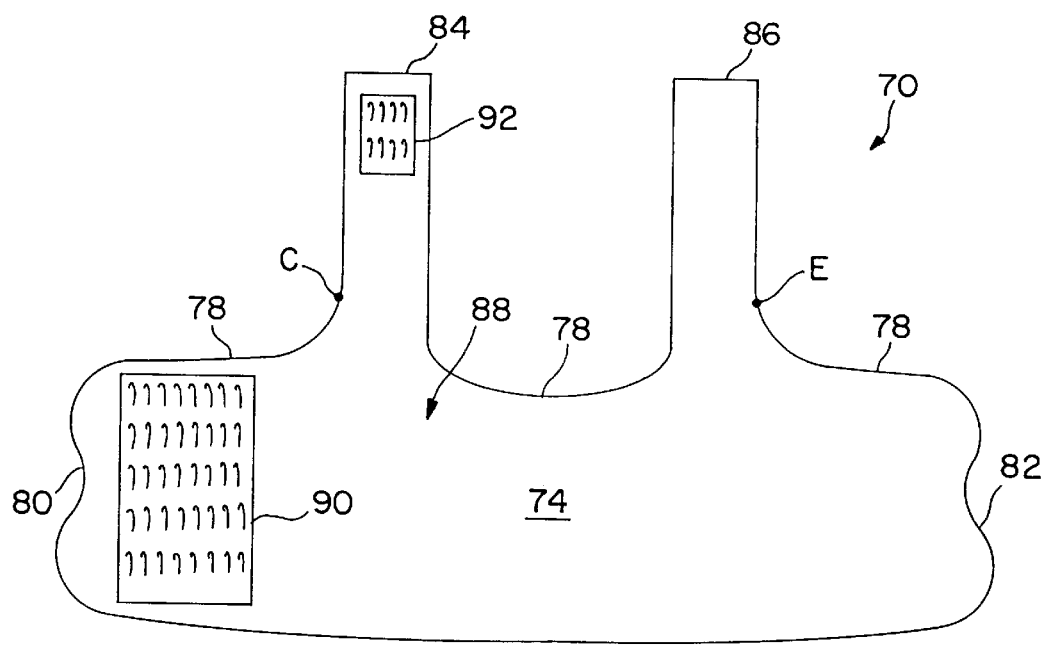
FIG. 8 is an interior plan view of a foot portion of the bootie of FIG. 7.
Figure 9:
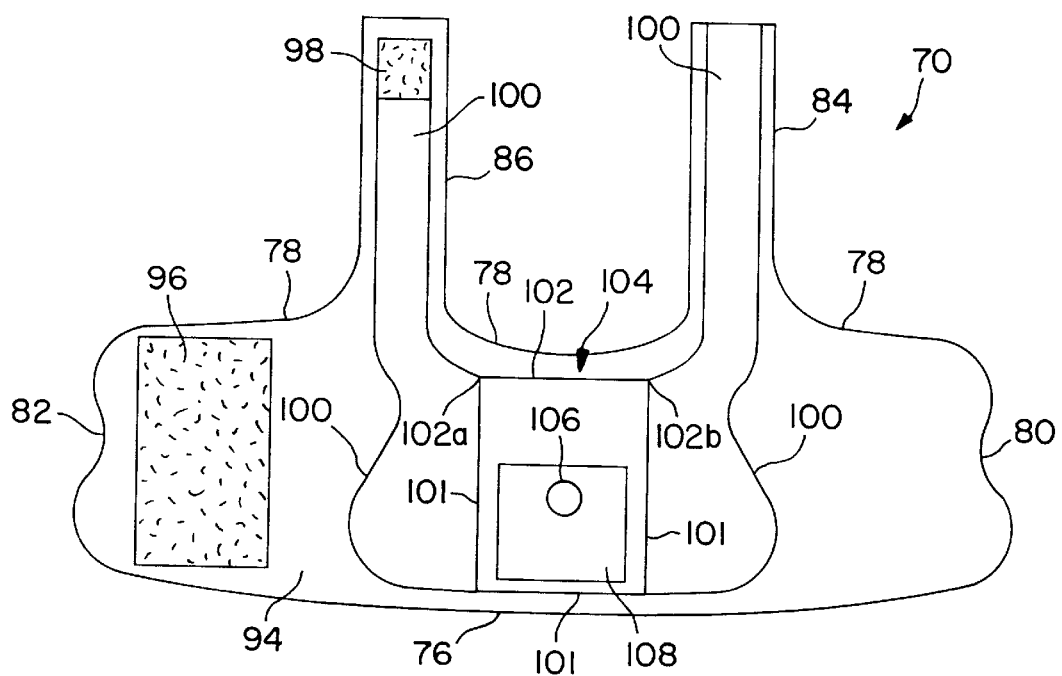
FIG. 9 is an exterior plan view of a foot portion of the bootie of FIG. 7.
Figure 11:
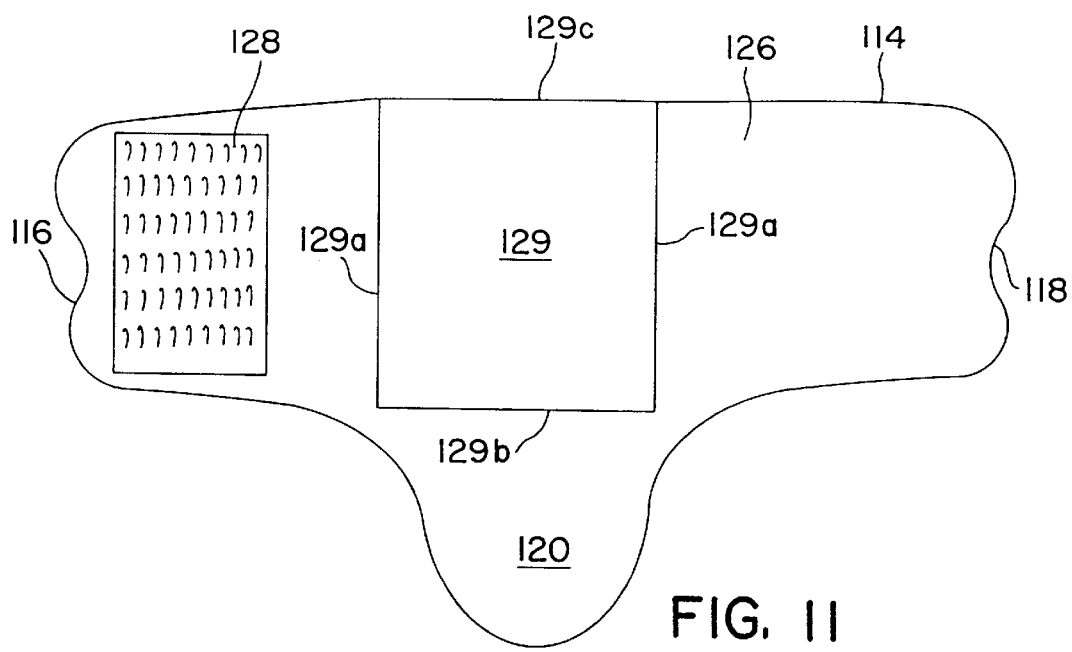
FIG. 11 is an exterior plan view of a leg portion of the bootie of FIG. 7.
Figure 10:
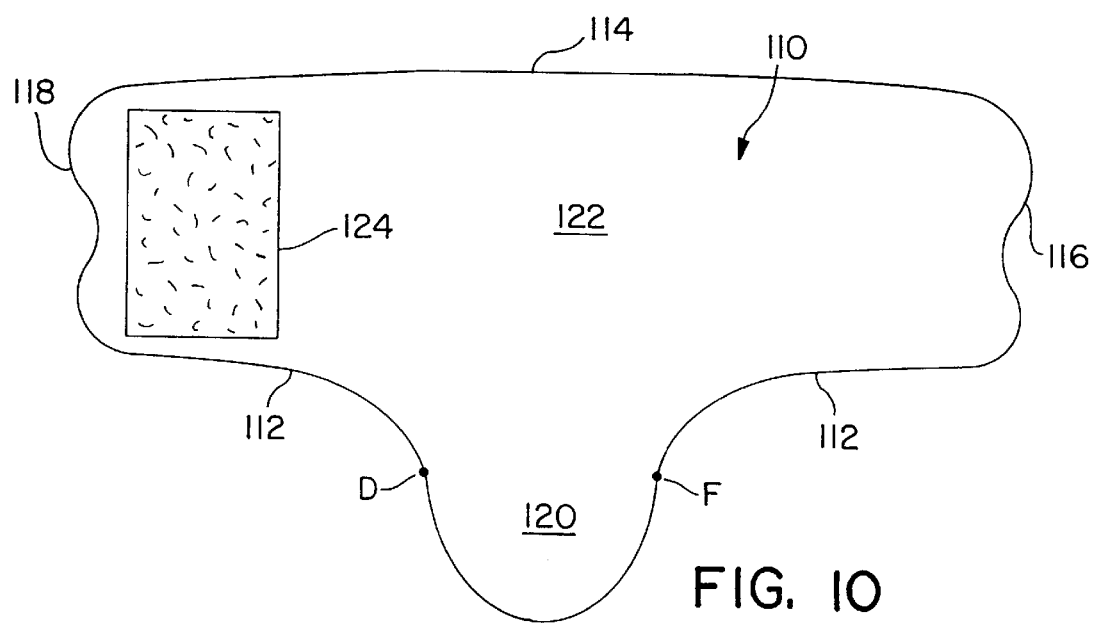
FIG. 10 is an interior plan view of a leg portion of the bootie of FIG. 7.

The bootie 14 includes a foot portion 70 and a leg portion 72 that are preferably attached to one another. FIGS. 8 and 9 are interior and exterior plan views, respectively, of the foot portion 70 laid out in flat or planar orientation. FIGS. 10 and 11 are interior and exterior plan views, respectively, of the leg portion 72 laid out in flat or planar orientation.

The foot portion 70 includes a substantially rectangular main body portion 74 having side edges 76 and 78 and end edges 80 and 82. A pair of strap portions 84 and 86 extend substantially perpendicularly away from the side edge 78 of the body portion 74. Turning to FIG. 8, interior surface 88 of the foot portion 70 preferably includes a section of loop material 90 secured thereto, as by stitching, for releasable securement of the foot portion about the splint 12 and the foot of the user, as will be explained more fully below. The interior surface of the strap 84 also preferably a section of loop material 92 secured thereto, as by stitching, for releasable securement of the strap 84 to the strap 86, as will be explained below.

With reference to FIG. 9, exterior surface 94 of the body portion 74 includes a section of hook material 96 secured thereto, as by stitching, for mating with the loop material 90 when the orthosis 10 is installed on a patient. Likewise, the exterior surface of the strap 86 includes a section of hook material 98 secured thereto, as by stitching, for mating with the loop material 92 of the strap 84. A section of nylon material 100 is preferably secured as by stitching 101 to a portion of the exterior surface 94 as shown in FIG. 9 for providing a durable and stain resistant exterior surface. A portion of the nylon material, particularly edge 102 extending between points 102a and 102b is not secured to the surface 94 so as to define a pocket 104 for slidably positioning over the foot contacting portion 20 of the splint 12. An aperture 106 extends through the pocket 104 for receiving the end nut 62 described above.

A non-skid material 108 is provided on the exterior of the pocket 104 for providing a surface having a relatively high coefficient of friction for contacting the toe support 16 when it is installed on the splint 12 to inhibit rotation of the toe support 16 relative to the splint 12. A preferred non-skid material 108 is synthetic rubber secured as by stitches onto the exterior of the pocket 104.

Turning to FIGS. 10 and 11, the leg portion 72 includes a substantially rectangular body portion 110 having side edges 112, 114 and end edges 116, 118. A tongue 120 extends substantially outwardly from a central portion of edge 112. The tongue 120 preferably incorporates padding 121 (FIG. 7) therein or thereon for additional patient comfort. Interior surface 122 of the leg portion 72 preferably includes a section of loop material 124 secured thereto adjacent the edge 118, as by stitching, for releasable securement of the leg portion about the splint 12 and the leg of the user, as will be explained more fully below. Exterior surface 126 of the leg portion 72 includes a section of hook material 128 secured thereto, as by stitching, for mating with the loop material 124 when the splint is installed on a patient. A pocket 129 is provided on the exterior surface 126 for receiving the leg portion 22 of the splint 12. The pocket is formed by stitched edges 129a and open edge 129b. A portion of material sufficient to provide the pocket 129 preferably extends from the body potion 110 and is folded over a fold line 129c and secured along the edges 129a.

The foot portion 70 and the leg portion 72 are secured together with the interior surfaces thereof facing in generally the same manner by securing (as by stitching) point C on the strap 84 of the foot portion 70 to point D of tongue 120 of the leg portion 72 and by securing point E on the strap 86 of the foot portion 70 to point F of tongue 120 of the leg portion 72.

Toe Support 16

Figure 12:
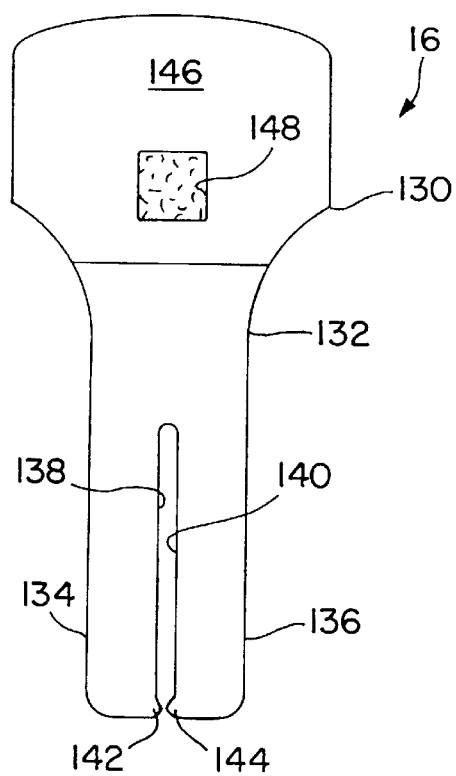
FIG. 12 is a bottom plan view of a toe support suitable for use in the orthosis of the present invention.
Figure 13:
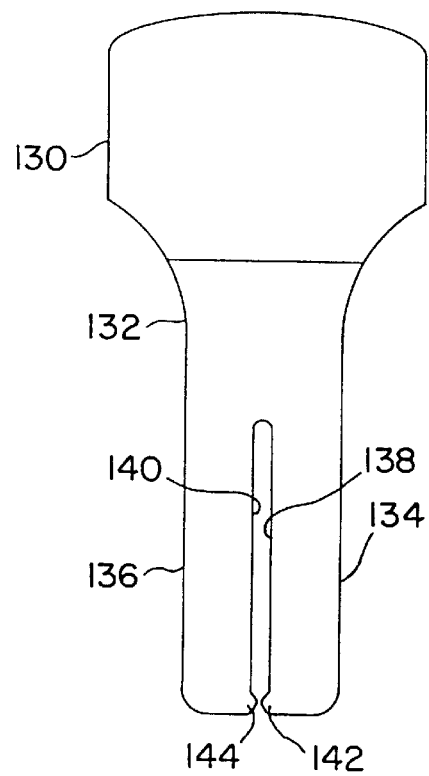
FIG. 13 is a top plan view of the toe support of FIG. 12.
Figure 14:
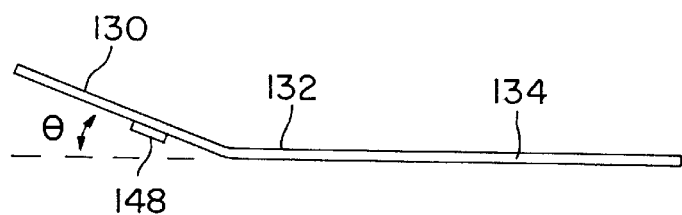
FIG. 14 is a side plan view of the toe support of FIG. 13.
Figure 22:
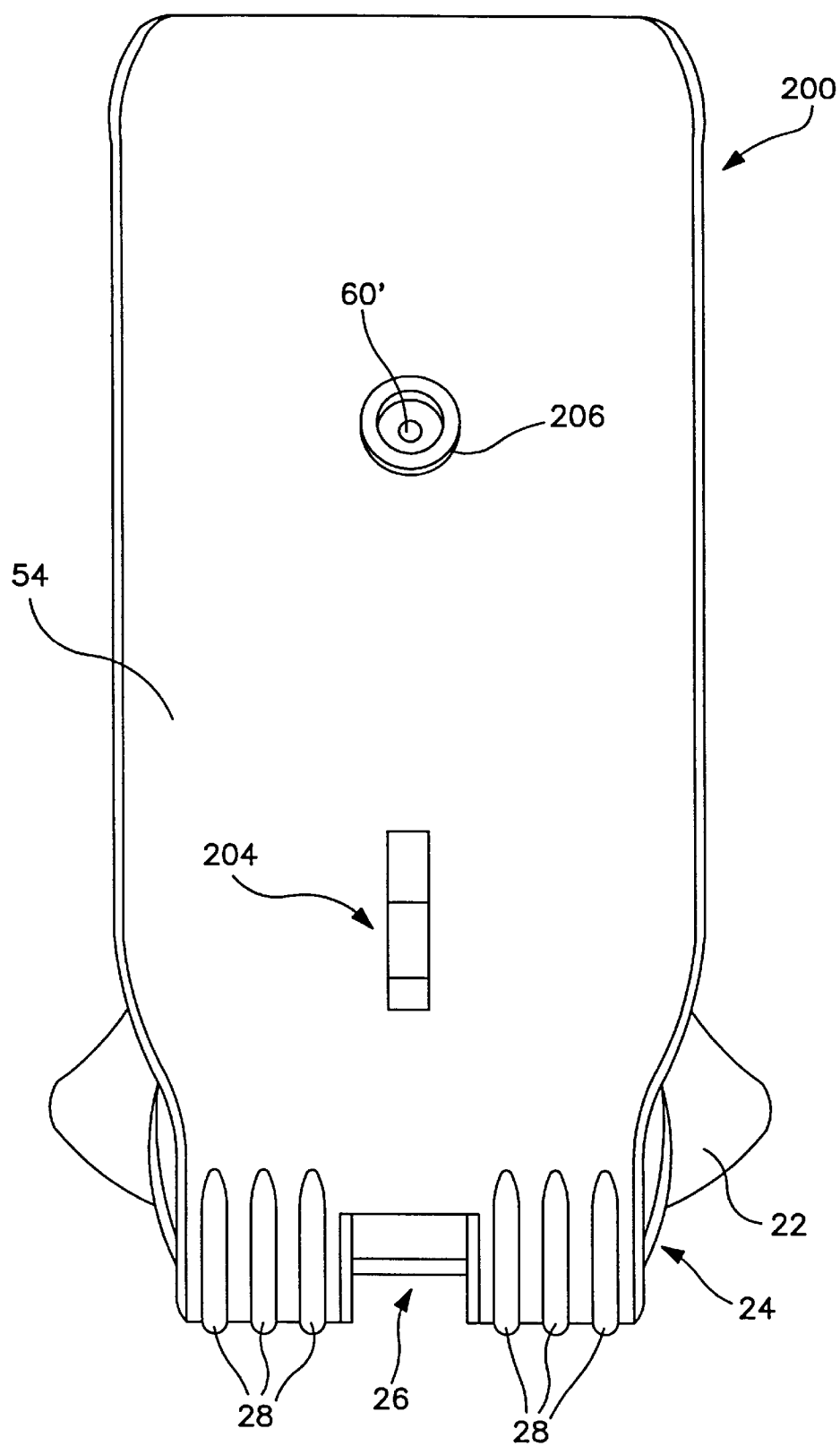
FIG. 22 is a bottom view of an alternate embodiment of a splint for use in the orthosis of the present invention.
Figure 23:
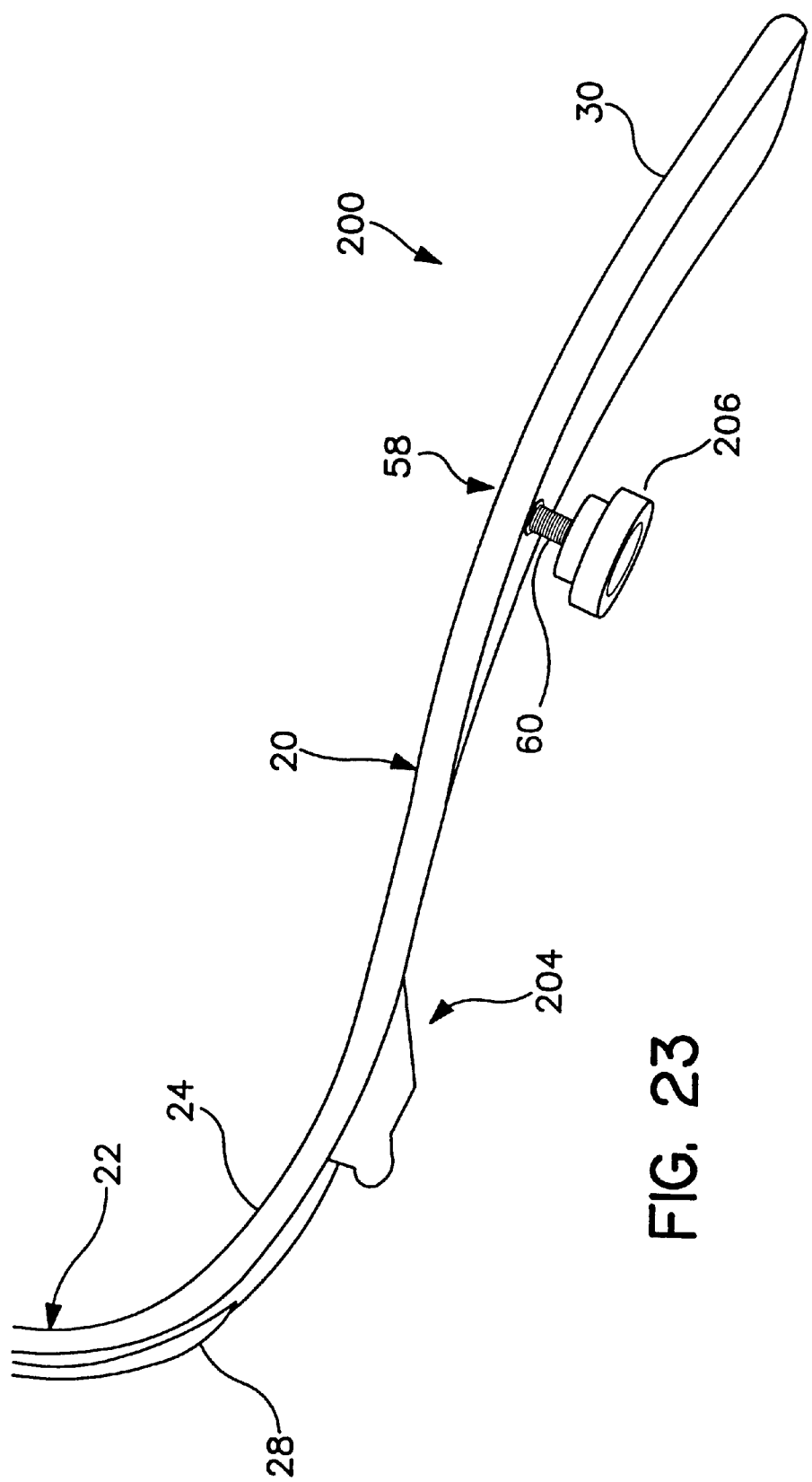
FIG. 23 is a side view of a portion of the splint of FIG. 22.

Turning to FIGS. 12–14, the toe support 16 is preferably of one-piece molded plastic construction and includes a head 130 connected by a neck 132 to legs 134 and 136. A preferred plastic material is polypropylene. The toe support 16 supports the toes of the patient in a desired orientation relative to the foot of the patient.

The head 130 preferably extends upwardly at an angle θ of from about 10° to about 30° away from the plane of the neck 132 and legs 134, 136. Interior edges 138 and 140 of the legs 134 and 136, respectively, are spaced apart a distance to enable them to snugly grip the mounting bolt 60 when the toe support 16 is mounted on the splint 12. For a bolt 60 having a diameter of about 3/16 inch, the legs 134 and 136 are preferably spaced about 1/4 inch apart.

To inhibit the toe support 16 from sliding past the mounting bolt 60, the ends of the legs 134 and 136 preferably include points 142 and 144 which extend toward one another to reduce the space between the legs 134 and 136 so that the bolt 60 cannot slide past the points 142 and 144. For a 3/16 inch bolt, the points are preferably spaced about 1/16 apart. When removing the toe support 16 from the splint 16, sufficient pressure may be exerted by the patient to bear the points 142 and 144 against the bolt 60 so as to cause the legs 134 and 136 to flex and spread apart and pulled past the mounting bolt 60, thereby permitting the toe support 16 to be removed from the splint.

A lower surface 146 of the head 130 preferably includes a section of loop material 148 attached thereto, as by adhesive, for mating with hook material provided on a corresponding interior portion of a fabric cover 150 (FIG. 2) configured to be slipped over the head 130 to serve as padding to improve patient comfort.

Sole Member 18

With reference to FIGS. 15–17, the sole member 18 has a substantially rectangular body 160 having an upper surface 162 opposite a lower, floor contacting, surface 164. The body 160 is preferably of molded rubber construction and has a thickness of from about 1/4 inch to about 3/4 inch, most preferably about 1/2 inch. The surface 164 is preferably rugose or otherwise textured to provide a surface that resists slipping when a patient is standing or ambulating.

A key-shaped slot 166 including a circular portion 168 and an elongate portion 170 extends between the surfaces 162 and 164 to provide clearance for the bolt 60 and end nut 62 during installation or removal of the sole member 18 from the splint 12. In this regard, a plate 172 preferably made of a substantially rigid material such as molded plastic, preferably ABS plastic having a thickness of from about 1/16 to about 3/16 inch, most preferably about 1/8 inch. The plate may be secured, as by adhesive, to the surface 162. The plate 172 includes a key shaped slot 174 having a circular portion 176 and an elongate portion 178 extending there through. The slot 174 is smaller than the slot 166 and is positioned so that it is substantially aligned with the slot 166. As will be noted, the slots 166 and 174 are reversed from one another, with the elongate portions 170 and 178 extending in opposite directions from one another. The circular portion 176 is sized slightly larger than the nut 62 for permitting its passage there through and the elongate portion 178 is sized just slightly larger than the bolt 60 so that it may be slidably, yet snugly, received therein.

A cutout 180 is defined on rear edge 182 of the plate 172 for snugly receiving the correspondingly shaped projection 56 located on the lower surface 54 of the splint 12. The cutout 180 and the projection 56 cooperate to enable the projection 56 to be slidably inserted into the cutout during installation of the sole member 18 onto the splint 12 to inhibit rotational and axial movement of the sole member 18 relative to the splint 12.

In this regard, and with reference to FIGS. 18a and 18b, the projection 56 includes a body portion 184 extending from the surface 54 of the splint 12 and slidingly receivable between walls 186 and 188 of the cutout 180. Lowermost portion 190 of the body portion 184 defines a pair of shoulders 192 and 194. The shoulders 192 and 194 are matingly receivable between sidewalls 196 and 198 of the cutout 180.

The body portion 184 preferably has a height h of from about 1/16 to about 1/4 inch, most preferably about 1/8 inch, a length l of from about 1/4 to about 3/4 inch, most preferably about 1/2 inch, and a width w of from about 1/4 to about 3/4 inch, most preferable about 1/2 inch. The span between the walls 186 and 188 is preferably from about 3/16 to about 5/16 inches, most preferably about 1/4 inches.

Assembly and Use

Returning now to FIG. 2 and with additional reference to FIGS. 19–21, the orthosis 10 may be assembled by first installing the bootie 14 on the splint 12 and then installing the toe support 16 on the bootie/splint assembly. The bootie 14 may be installed on the splint 12 by slipping the pocket 129 over the leg portion 22, bending the leg portion 22 toward the foot portion 20 and slipping the pocket 104 over the foot portion 20 and passing the end nut 62 (installed on the bolt 60) and cover 64 through the aperture 106 of the pocket 104. The end nut 62 is loosened, if necessary, to permit installation of the toe support 16 by sliding the toe support 16 so that the bolt 60 is captured between the legs 34 and 36 of the toe support 16 (FIG. 20). The end nut 62 is then tightened until it is snugly against the toe support 16.

The thus assembled orthosis may then be installed on the foot/leg of a patient in bed. If desired, the sole member 18 may thereafter be installed for floor contact, such as for ambulation by the patient (FIG. 20). This may be accomplished by loosening the nut 62 an amount to slightly greater than the thickness of the plate 172 of the sole member 18. The sole member 18 is then positioned with the surface 162 thereof adjacent the legs 34 and 36 of the toe support 16 and the nut 62 and cover 64 within the circular portion 176. Optionally, the toe support 16 may be removed prior to installing the sole member 18. Pressure is then exerted to slide the sole member 18 toward the bend 24 of the splint 12 so that the projection 56 engages the aperture 180 and bolt 60 is captured within the slot 178 of the plate 172. The nut 62 is then tightened until snug.

The assembled foot orthosis is thus configured for ambulation, wherein the sole member 18 contacts the floor. The sole member 18 is thereafter removed prior to the patient's return to bed. The installation and removal of the sole member 18 may be accomplished by the patient, depending on his general physical ability, or by an attendant. It is preferred that the sole member 18 be installed and removed by an attendant, with the patient sitting up on the bed with the patient's leg hanging over the side of the bed.

As will be appreciated, a significant aspect of the invention relates to the provision of a foot orthosis having a sole member that can be quickly and conveniently installed or removed and that is attached in a manner suitable for ambulation by the patient. The capture of the bolt 60 within the slot 178 and the capture of the projection 56 within the cutout 180 enable the sole member to be reliably and easily attached to the splint 12 in a manner sufficient to enable the patient to ambulate without the sole member 18 detaching from the splint 12 or rotating or otherwise moving relative to the splint 12 during ambulation. Following ambulation, the structure enables quick and convenient removal of the sole member 18 for return of the patient to bed.

FIGS. 22–31

With reference now to FIGS. 22–31, there is shown another embodiment of a splint 200 and a sole member 202 removably attachable to the splint 200. The splint 200 and the sole member 202 are compatible with the previously described bootie 14 and toe support 16 and can be substituted for the splint 12 and the sole member 18 to provide the orthosis 10.

The splint 200 is substantially identical to the splint 12, except that it includes a projection 204 in place of the nib 56 of the splint 12 and an end member 206 that replaces the nut 62. In this regard, reference numerals associated with the splint 12 have been ascribed to the splint 200 for the parts common between the splint 12 and the splint 202.

Figure 26:
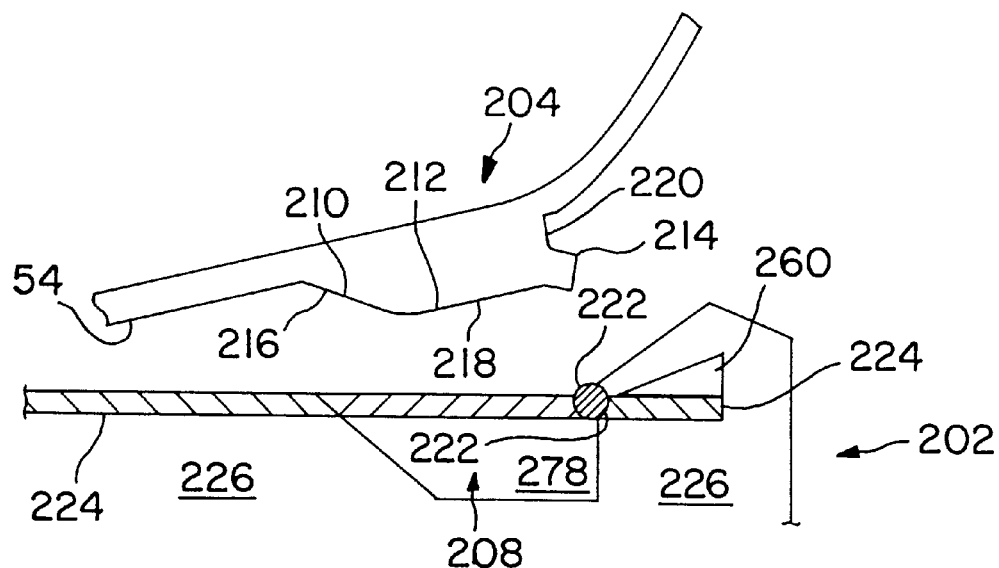
FIGS. 26 and 27 are close-up views showing connection of the sole member of FIG. 24 to the splint of FIG. 22.
Figure 27:
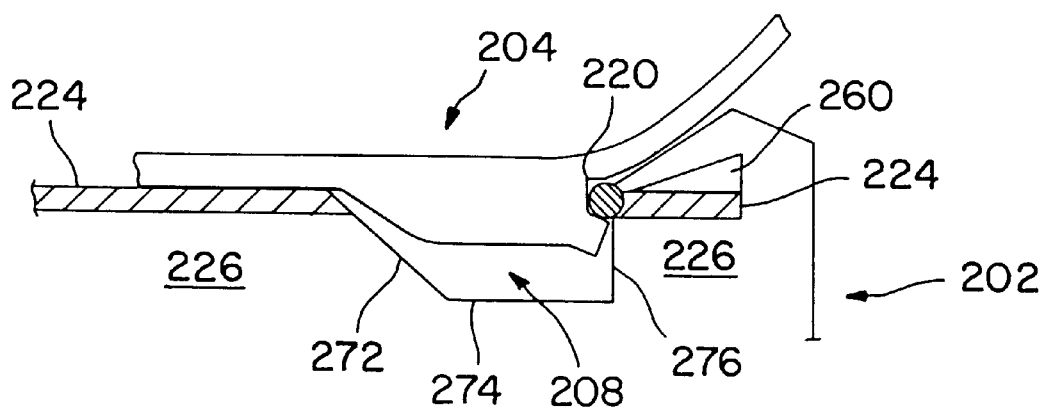

The end member 206 is preferably fixedly attached to mounting bolt 60 as by a fastener 60' so that the locking nut 66 is not needed. The projection 204, like the nib 56, is positioned to engage a corresponding receptacle 208 on the sole member 202, as shown in FIGS. 26 and 27.

The projection 204 has a sloped front portion 210, a substantially flat middle portion 212, and a projecting rear portion 214. Surface 216 of the front portion 210 slopes away from the surface 54 of the splint 212 and surface 218 of the middle portion 212 is substantially parallel to the surface 54. The rear portion 214 projects from the middle portion 212 in an angular direction away from the surface 54 to define a notch 220 between the rear portion 214 and the surface 54 of the splint. The notch 220 engages a ledge 222 extending from the sole member 202 adjacent the receptacle 208, as will be explained more fully below.

Figure 28:
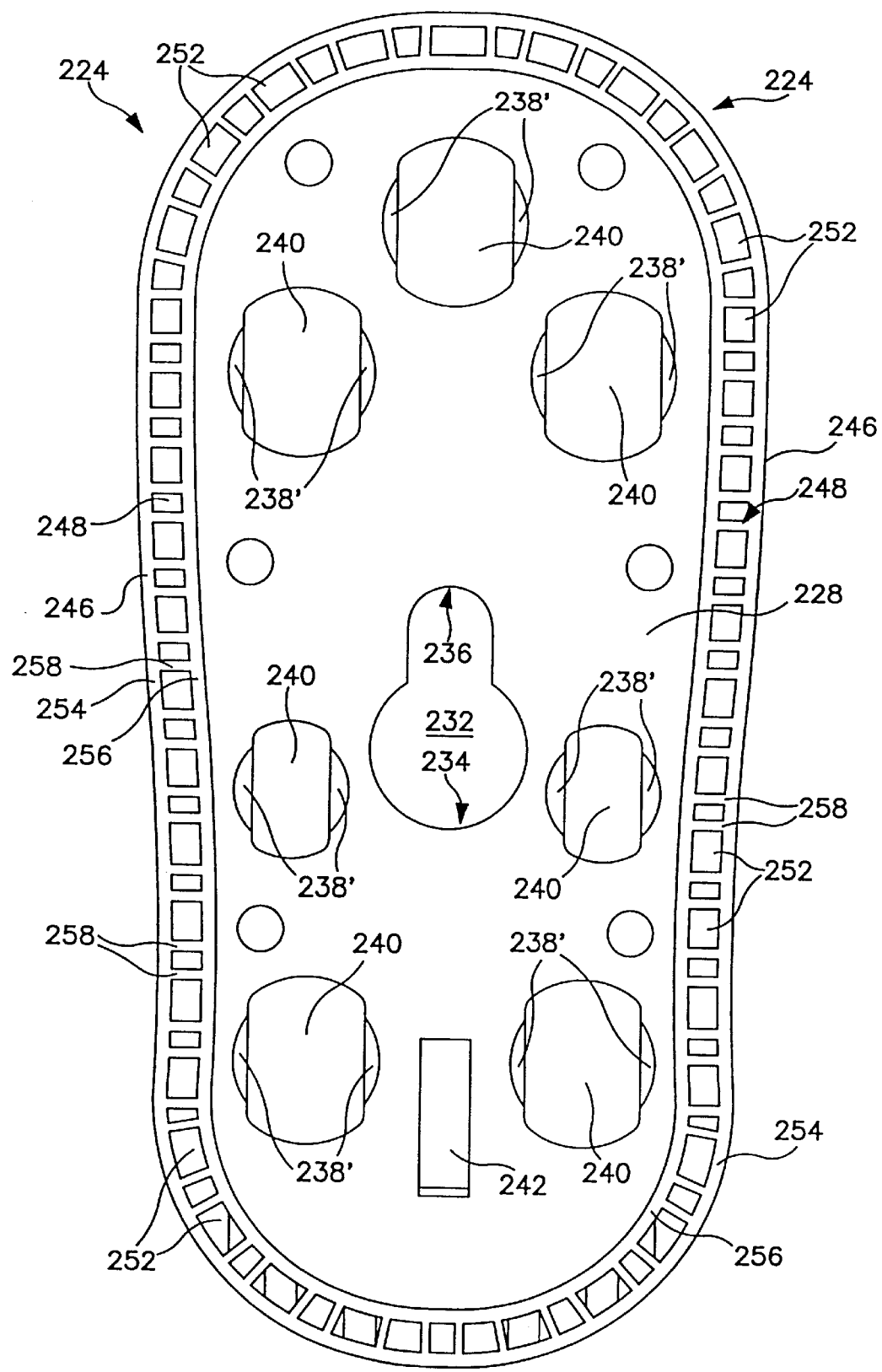
FIG. 28 is a bottom plan view of a plate component of the sole member of FIG. 24.
Figure 29:
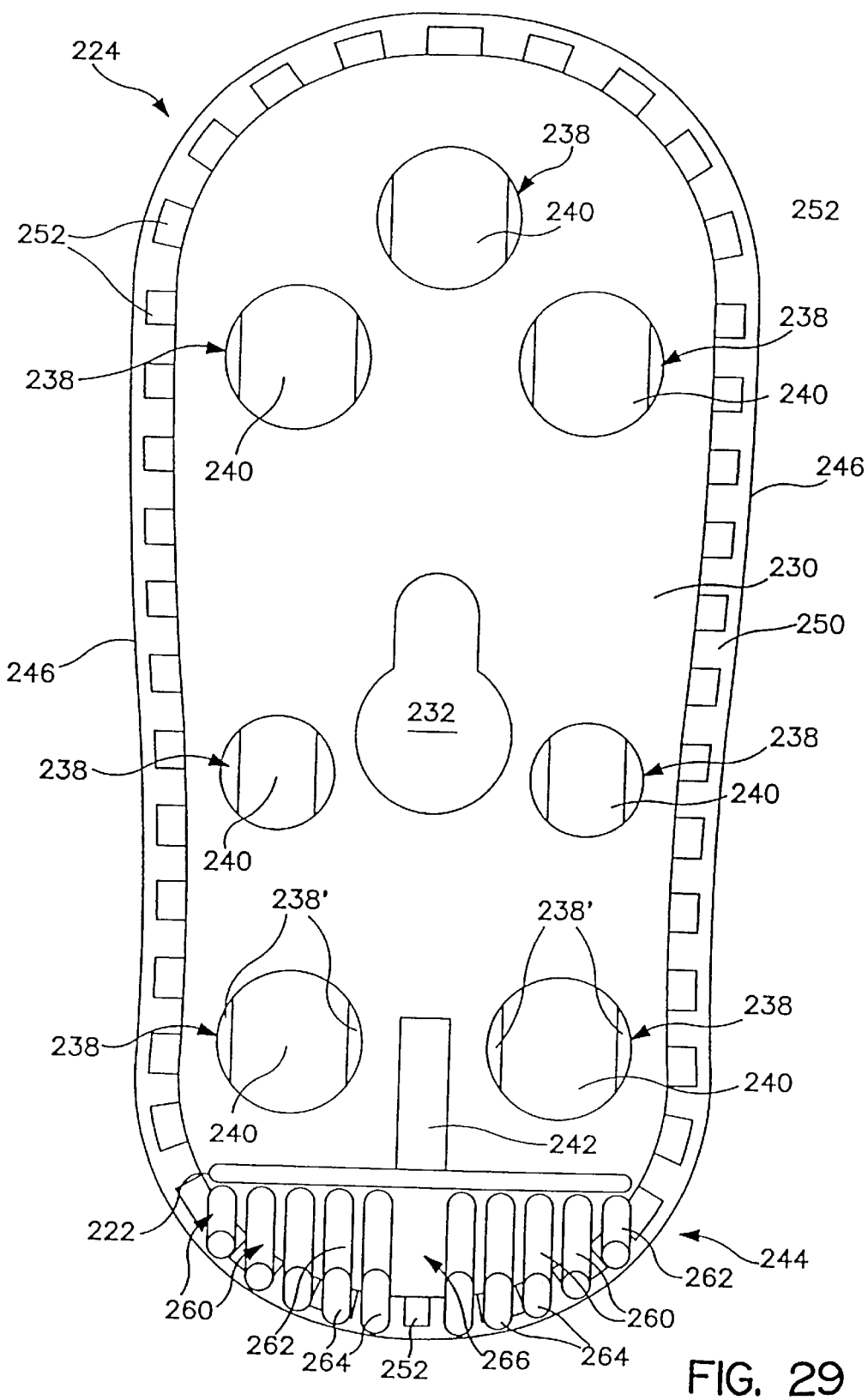
FIG. 29 is a top plan view of the plate component of FIG. 28.
Figure 30:
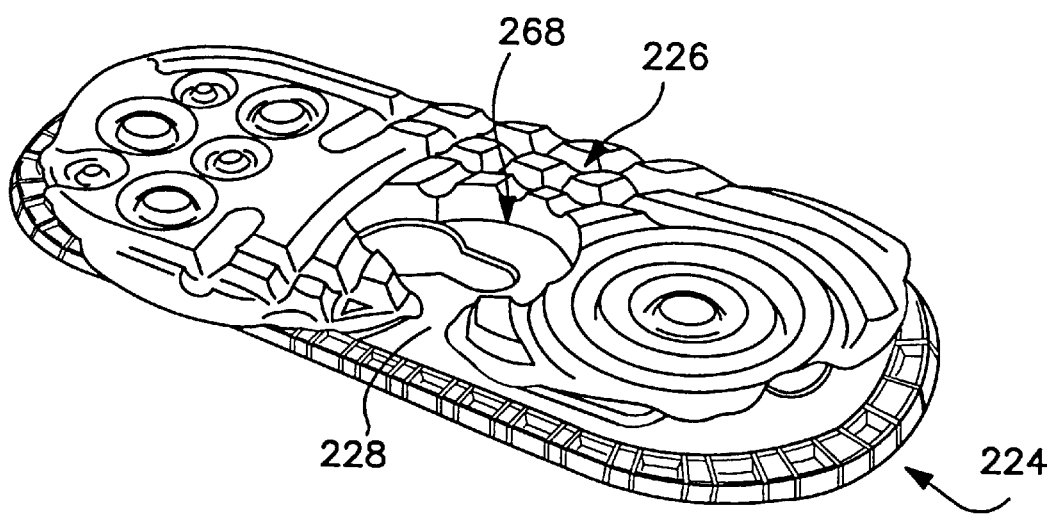
FIG. 30 is a bottom perspective view showing the relationship between a polymeric sole material and the plate component.
Figure 31:
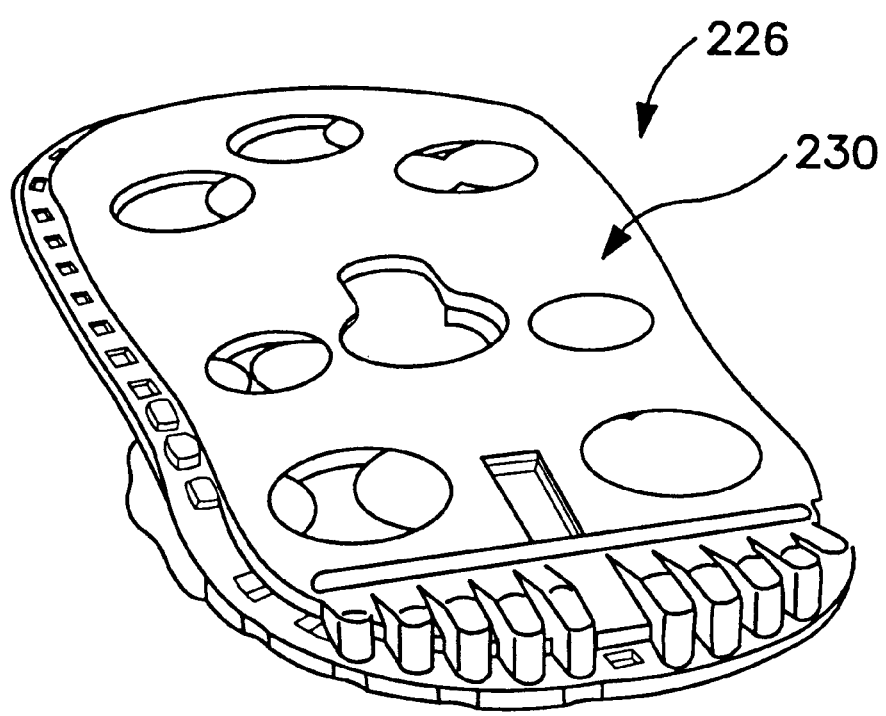
FIG. 31 is a top perspective view showing the relationship between a polymeric sole material and the plate component.
Figure 32:
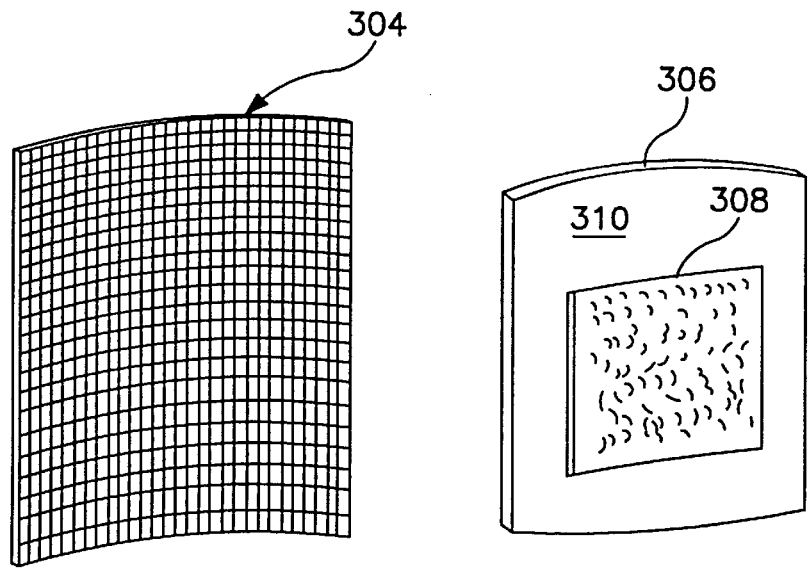
FIG. 32 is an exploded perspective view showing a thermal pouch for use with the orthosis of the present invention.
Figure 33:
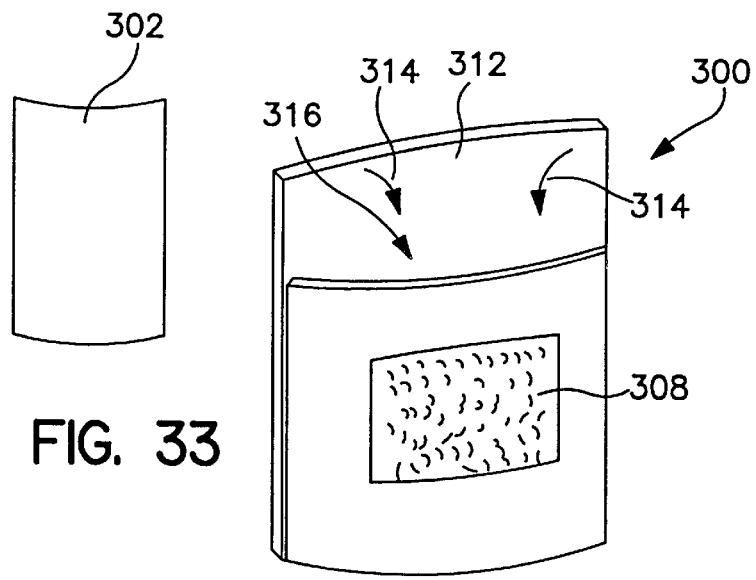
FIG. 33 is a front perspective view of an assembled thermal pouch.
Figure 34:
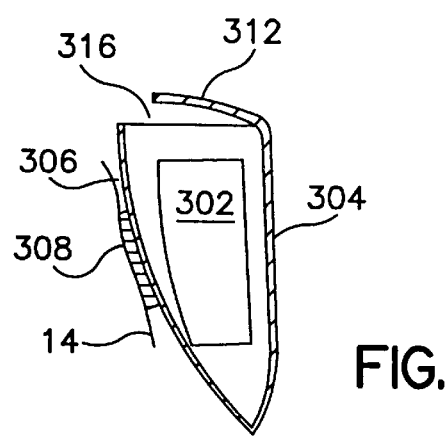
FIG. 34 is a cross-sectional side view of the pouch of FIG. 29.

With further reference now to FIGS. 28–31, the sole member 202 has an inner plate or core member 224 (See, FIGS. 28–29) onto which is applied a sole material 226 (See, FIGS. 30–31). The material 226 is preferably a rubber or rubber-like sole material of the type used in the manufacture of shoe soles (e.g, natural or synthetic rubber, nylon and like polymeric materials) molded onto the member 224.

Turning now to FIGS. 28 and 29, the core member 224 is preferably made of a substantially rigid material such as molded plastic, preferably ABS plastic having an overall thickness of from about ⅛ to about ¼ inch, most preferably about 3/16 inch. The member 224 has opposite substantially planar surfaces 228 and 230, with a key shaped slot 232 having a circular portion 234 and an elongate portion 236 extending between the surfaces 228 and 230 for cooperating with the nut 60 and end member 206 for installing the sole member 202 onto the splint 200.

A plurality of apertures, preferably circular apertures 238, extend between the surfaces 228,230 of the member 224. Cross-members 240 located adjacent surface 228 extend across each of the apertures 238, leaving open portions 238' of the apertures 238. Elongate, preferably rectangular aperture 242 extends between the surfaces 228,230 adjacent heel end 244 of the member 224 and provides access to the receptacle 208 in the assembled sole member 202.

A ledge 246 having opposite surfaces 248 and 250 is preferably provided around the perimeter of the member 224. The ledge 246 is preferably vertically offset from the member 224 such that the surface 250 of the ledge 246 is substantially co-planar with the surface 228 of the core member 224 and the plane of the surface 248 of the ledge 246 is offset from the surface 228 of the core member 224 by an amount corresponding to the thickness of cross members 240, such as about 1/16 inch.

A plurality of apertures 252 extend through the thickness of the ledge 246 and are preferably uniformly spaced apart from one another. The surface 250 of the ledge 246 is preferably smooth. Rims 254, 256 rise from the surface 248 and extend around the ledge 246 on opposite sides of the apertures 252. Raised ribs 258 extend between the rims 254, 256 to frame each of the apertures 252.

Figure 29A:
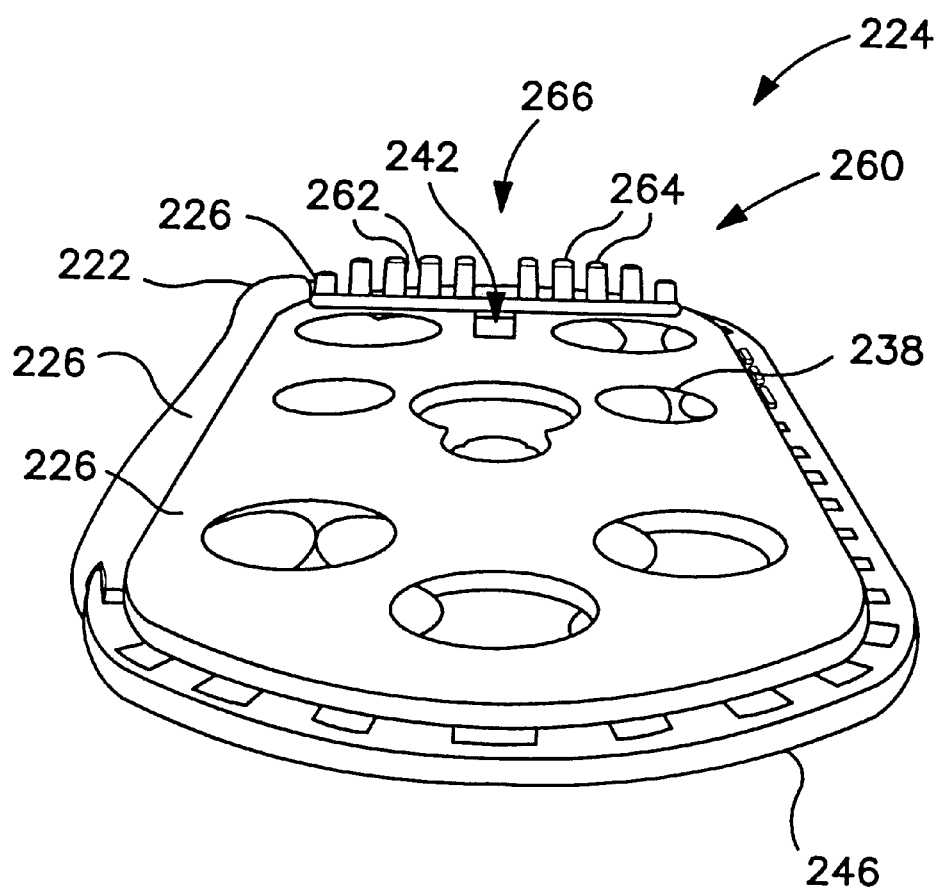
FIG. 29a is a perspective view showing a top heel end of the plate component.

A plurality of sloped ribs 260 extend from the surface 230 of the surface 230 toward the back of the member 224 adjacent the heel end 244. Each of the ribs 260 has a sloped surface 262 that terminates at a flat surface 264, as best seen in FIG. 29a. A ribless space 266 is provided between the ribs 260 adjacent the aperture 242.

Figure 24:
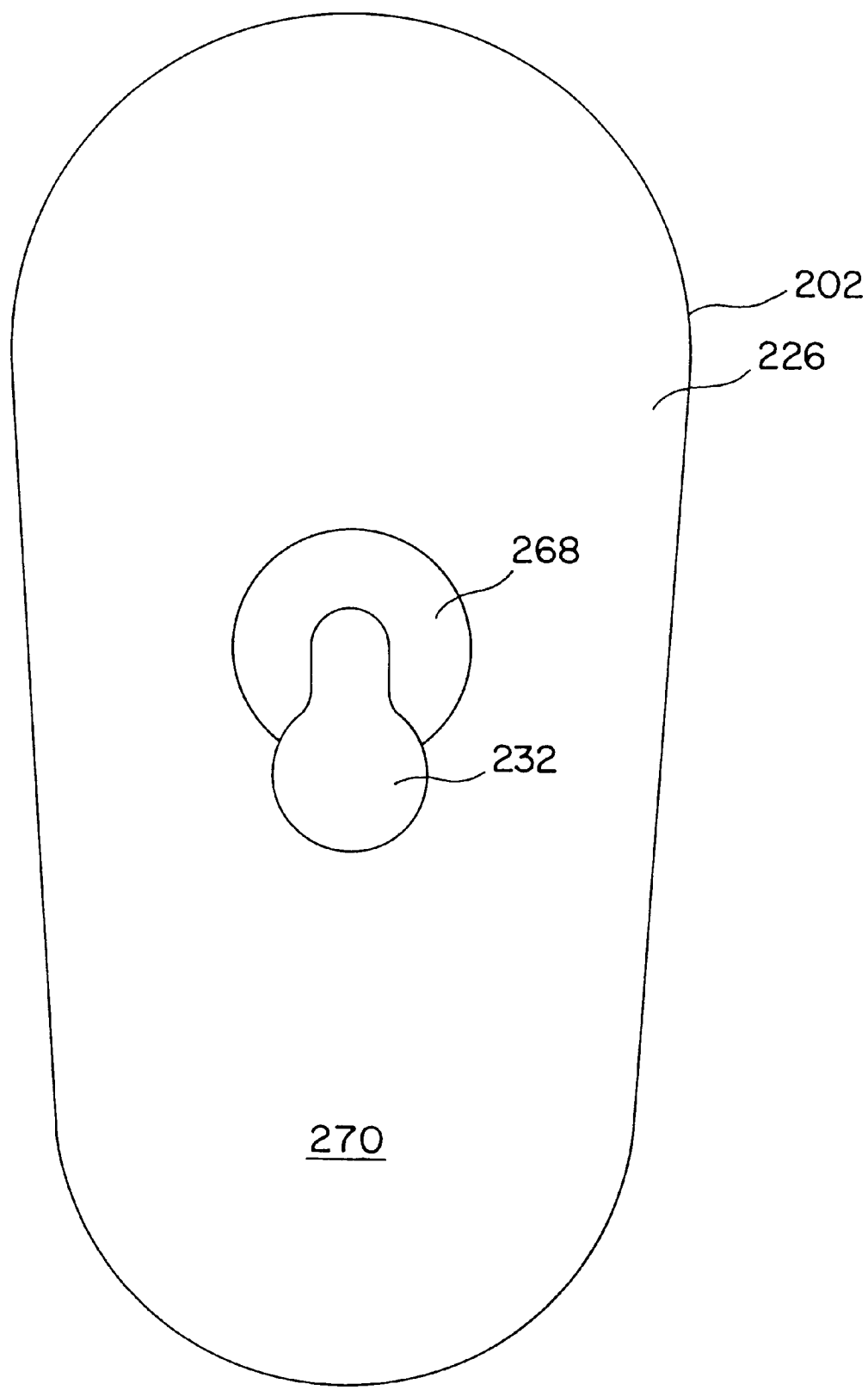
FIG. 24 is a bottom plan view of another embodiment of a sole member suitable for use with the splint of FIG. 22.
Figure 25:
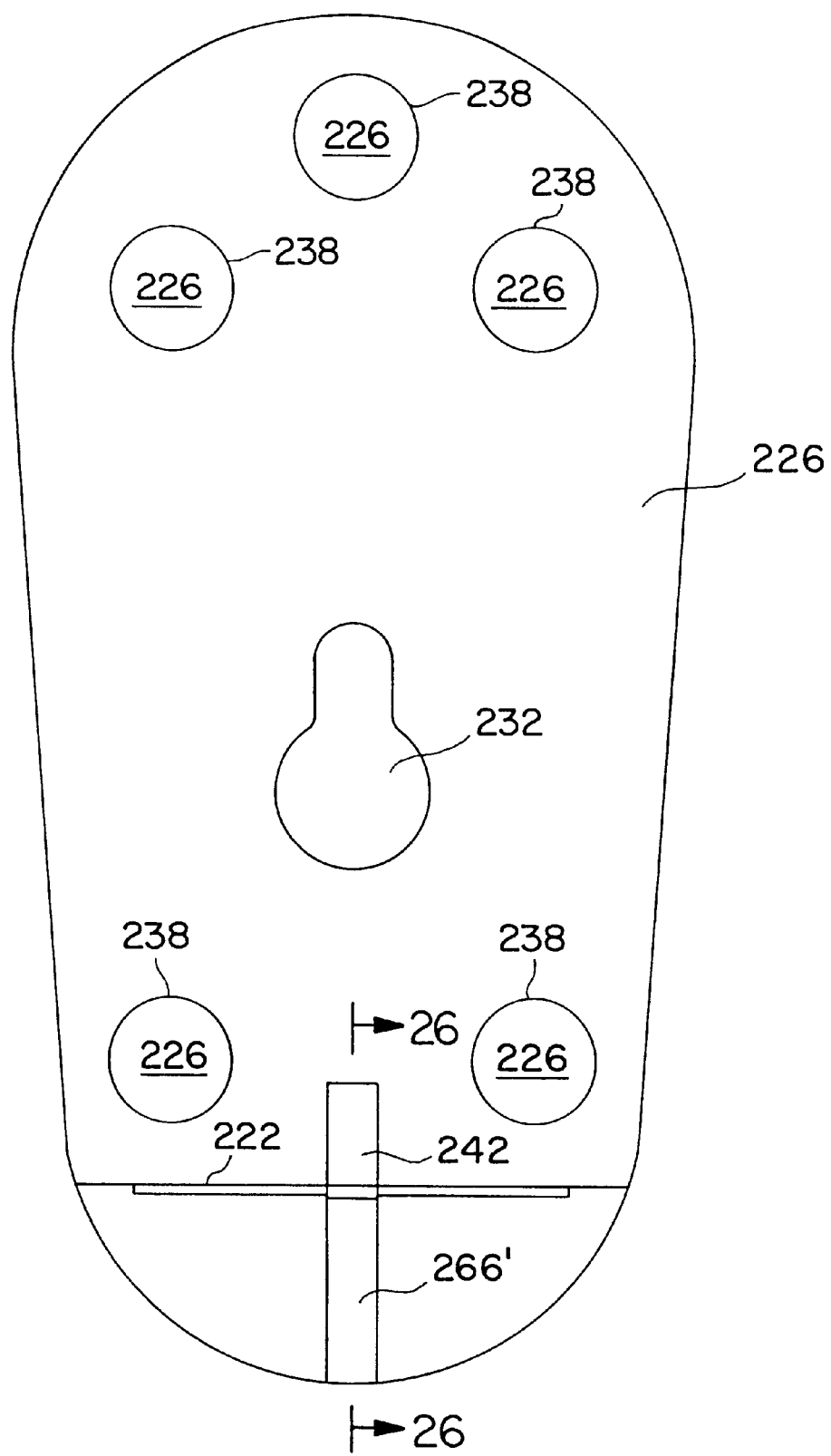
FIG. 25 is a top plan view of the sole member of FIG. 24.

With reference to FIGS. 24,25, 30 and 31, the material 226 is preferably molded onto the core member 224 using known molding techniques. The material 226 is applied so that on the side of the surface 228 it covers the surfaces 228 and 248, except for an open area 268 surrounding the slot 232 (FIG. 24). On the side 230 of the core member 226, the material 226 fills the apertures 238 and covers the surface 250 of the ledge 246 such that the material 226 is flush with the surface 230. The material 226 also covers the ribs 260, except adjacent the area 266 of the core member 224 so as to define channel 266'.

As will be appreciated, the apertures 238' and 252 and the ribs 260 provide topography for the material 226 to surround so that the sole member 202 is a composite or unitary part to inhibit separation of the material 226 from the member 224. In addition, the exposed surface 270 of the resulting molded part is preferably contoured in the manner of a shoe sole, preferably having a traction enhancing topography. Material is either subsequently removed from adjacent the aperture 242 or is stopped from occupying an area corresponding to the receptacle 208 so as to result in an open area that defines the receptacle 208. In this regard, and with additional reference now to FIGS. 27 and 28, the receptacle 208 includes sloped front-end wall 272, bottom 274, rear-end wall 276, and opposite sidewalls 278.

The orthosis may be assembled by first installing the bootie 14 on the splint 200 and then installing the toe support 16 on the bootie/splint assembly in substantially the same manner as previously described for the orthosis 10 having splint 12, except there is no need for loosening the end nut 62, as it is replaced with the end member 206. The sole member 202 may thereafter be installed for floor contact, such as for ambulation by the patient. This may be accomplished by placing the surface 230 adjacent the surface 54 of the splint 200 and aligning the slot 232 with the end member 206 so that it extends therethrough. The projection 204 is preferably within the channel 266'. With the user's thumbs on either side of the member 206 and bearing against the opposite exposed surface 270, pressure is applied to urge the sole toward the heel end of the splint so that the elongate portion 236 of the slot 232 is proximate the mounting bolt 60 and the projection 204 is adjacent the receptacle 208. Pressure is then applied in the region of the heel end of the sole member 202 to snap fit the projection 204 into the receptacle. Removal may be accomplished by reversing the steps, wherein the heel end of the sole member is pulled oppositely from the splint to unsnap the projection 204 from the receptacle and then sliding the sole member so that the end member 206 will pass back through the slot 232.

FIGS. 32–34

In accordance with another aspect of the invention, there is provided a pouch 300 releasably attachable to the bootie 14. The pouch 300 is configured to receive a thermal pack 302, e.g., a cold or heat pack. The pouch 300 is preferably made by securing together, as by sewing, adjacent edges of material 304 and 306, and securing a portion of hook material 308 to an outer surface 310 of the material 306.

The material 304 is preferably slightly longer than the material 306 so that a lid portion 312 extends above the material 306 and is available to be folded over toward the material 306 in the direction of the arrows 314 and stuffed into the pouch 300 and against the pack 302 so as to provide some resistance to help maintain the pack 302 within the pouch. For example, if the patient were to lie down such that opening 316 to the interior of the pouch becomes downwardly inclined, gravity would tend to urge the pack 302 out of the pouch. The lid portion 312 can be stuffed into the opening 316 to provide resistance to maintain the pack 302 within the pouch.

The material 304 is preferably a mesh material for contacting against the skin of a patient. Examples of suitable mesh materials include polyester, nylon and the like which tend to wick away moisture. The mesh also is relatively thin and does not significantly insulate against heat transfer from the thermal pack 302 within the pouch 300 to the skin of the patient. The material 306 is preferably similar to that used for the bootie 14 and is readily engaged by the hook material 308 for releasably securing the pouch 300 to a portion of the bootie 14 adjacent to the area of the patient where thermal treatment is desired.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A foot orthosis, comprising:
   a splint including a foot contacting portion having a generally upwardly facing foot contacting surface opposite a generally downwardly facing lower surface;
   a fastener extending away from the lower surface of the splint;
   a projection extending away from the lower surface of the splint and having a sloped front portion, a substantially flat middle portion, and a rear portion projecting away from the middle portion in an angular direction away from the lower surface of the splint to define a notch between the rear portion and the lower surface of the splint;
   a covering material positioned to surround a portion of the foot contacting portion of the splint such that a first covering surface is adjacent to and facing away from the foot contacting surface of the splint and a second covering surface is adjacent to and facing away from the lower surface of the splint, the covering including an aperture there through for passage of the fastener;
   a sole member having a lower floor contact surface opposite an upwardly facing surface, the sole member including a mounting aperture extending between the lower floor contact surface and the upwardly facing surface for receiving at least a portion of the fastener, and a receptacle portion adjacent the upwardly facing surface of the sole member and configured for engaging the projection extending from the splint in a snap-fit relationship, the sole member being positionable adjacent to the second covering surface, with the projection snap-fit into the receptacle portion of the sole member and the fastener received within the mounting aperture of the sole member to secure the sole member against rotational movement relative to the splint and to releasably attach the sole member to the splint in a manner sufficient to enable ambulation by a patient wearing the foot orthosis.

2. The orthosis of claim 1, wherein the receptacle portion further includes a ledge portion for engaging the notch of the projection.

3. The orthosis of claim 1, wherein the fastener comprises an elongate member secured to the splint and having an end member fixedly secured thereto.

4. The orthosis of claim 1, wherein the sole member comprises a core member having first and second opposite surfaces with a slot including a circular portion and an elongate portion extending between the first and second surfaces of the core member, and a sole material molded onto the core member.

5. The orthosis of claim 4, wherein the sole material comprises a polymeric material.

6. The orthosis of claim 4, wherein the core member includes a plurality of apertures extending between the first and second surfaces and substantially surrounded by the polymeric material to inhibit separation of the polymeric material from the core member.

7. The orthosis of claim 1, further comprising a pouch member releasably securable to the covering material and configured for receiving a thermal pack.

8. The orthosis of claim 7, wherein the pouch member comprises a first portion of material and a second portion of material having adjacent sides thereof secured together to define a pocket configured to receive the thermal pack through an opening thereof defined between unsecured edges of the first and second portions of material, the first portion of material having a length greater than the length of the second portion of material to define a lid portion positionable over the opening, and a portion of a hook material attached to the first portion of material.

9. An orthosis comprising a splint, a sole member detachably connectable to a surface of the splint, a fastener extending from the surface of the splint, an aperture extending through the sole member for receiving the fastener, a projection extending from the surface of the splint and spaced apart from the fastener, the projection including a sloped portion, a substantially flat portion adjacent the sloped portion, and a contoured portion projecting away from the flat portion in an angular direction away from the surface of the splint to define a notch between the contoured portion and the surface of the splint, and a receptacle defined on the sole member for receiving the projection in a snap-fit relationship when the sole member is installed on the splint.

10. The orthosis of claim 9, wherein the receptacle includes a ledge portion for engaging the notch of the projection.

* * * * *